(12) United States Patent
Hajduch et al.

(10) Patent No.: US 8,465,936 B2
(45) Date of Patent: Jun. 18, 2013

(54) METHOD FOR DETERMINING THE SENSITIVITY OF PATIENTS SUFFERING FROM A CANCER DISEASE TO BIOLOGICAL THERAPY

(75) Inventors: Marian Hajduch, Moravsky Beroun (CZ); Marta Dziechciarkova, Olomouc (CZ); Lenka Radova, Otinoves (CZ); Marek Svoboda, Syrovice (CZ)

(73) Assignees: Univerzita Palackeho V Olomouci, Lekarska Fakulta, Olomouc (CZ); Masarykuv Onkologicky Ustav, Brno (CZ)

( * ) Notice: Subject to any disclaimer, the term of this patent is extended or adjusted under 35 U.S.C. 154(b) by 226 days.

(21) Appl. No.: 12/863,517

(22) PCT Filed: Jan. 23, 2009

(86) PCT No.: PCT/CZ2009/000006
§ 371 (c)(1),
(2), (4) Date: Sep. 20, 2010

(87) PCT Pub. No.: WO2009/092338
PCT Pub. Date: Jul. 30, 2009

(65) Prior Publication Data
US 2011/0014637 A1    Jan. 20, 2011

(30) Foreign Application Priority Data
Jan. 25, 2008   (CZ) .................................. PV 2008-40

(51) Int. Cl.
*G01N 33/574*   (2006.01)

(52) U.S. Cl.
USPC ........................................................ 435/7.23

(58) Field of Classification Search
None
See application file for complete search history.

(56) References Cited

PUBLICATIONS

Lyzogubov et al (Exp Oncol 2005, 27:141-144).*
Barlund et al (J national Cancer Institute, 2000, 92:1252-1259).*
Rojo et al (Clinical Cancer Research, Jan. 2, 2007, 13:81-89).*
Neve et al (Proc Amer Assoc Cancer Res, 2006, 47: abstract #3378).*
Noh et al (Clinical Cancer Research, 2004, 10:1013-1023).*
Fenton et al (The International Journal of Biochemistry and Cell Biology, 2011, 43:47-59).*
Cell Signaling technology ErbB/HER Signaling map, printed Feb. 2013.*

* cited by examiner

*Primary Examiner* — Laura B Goddard
(74) *Attorney, Agent, or Firm* — Notaro, Michalos & Zaccaria P.C.

(57) ABSTRACT

The invention relates to a method for determining the sensitivity of patients suffering from a cancer disease towards targeted biological therapy based on the inhibition of signaling pathways of the members of HER family (e.g., HER-1, HER-2, HER-3 and HER-4) by determining the expression of the biomarker S6 kinase or its post-translationally modified form or of the biomarkers of the activation of S6 kinase or their post-translationally modified forms in the tumor.

1 Claim, 14 Drawing Sheets

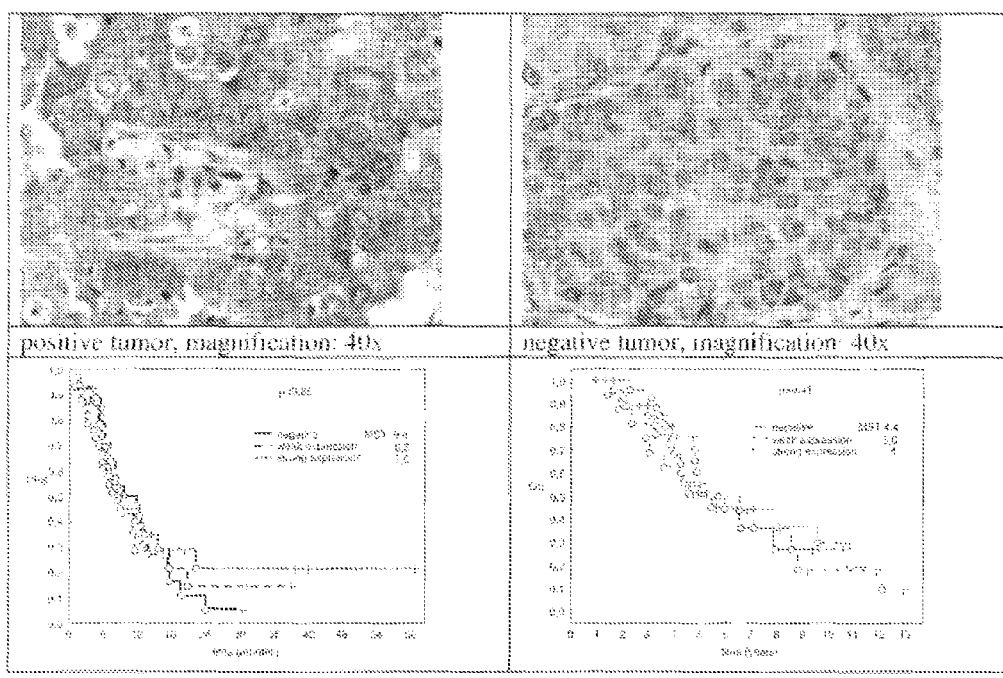
Fig. 1: Biomarker: total Act (pan) kinase; antibody: (11E7) rabbit mAb (Cell Signaling, USA)

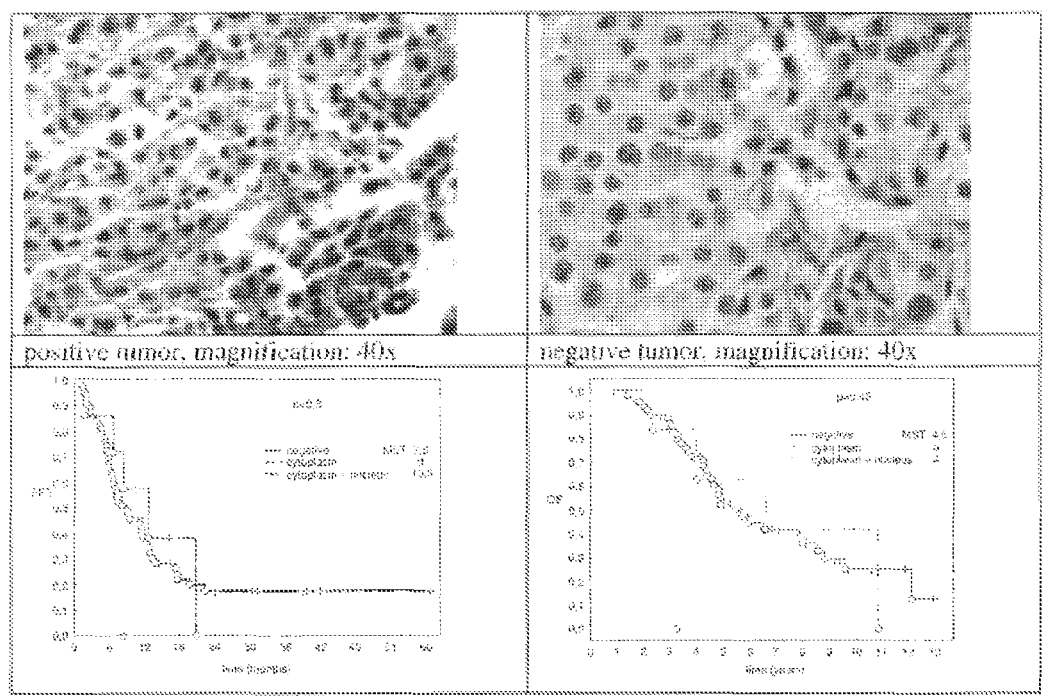

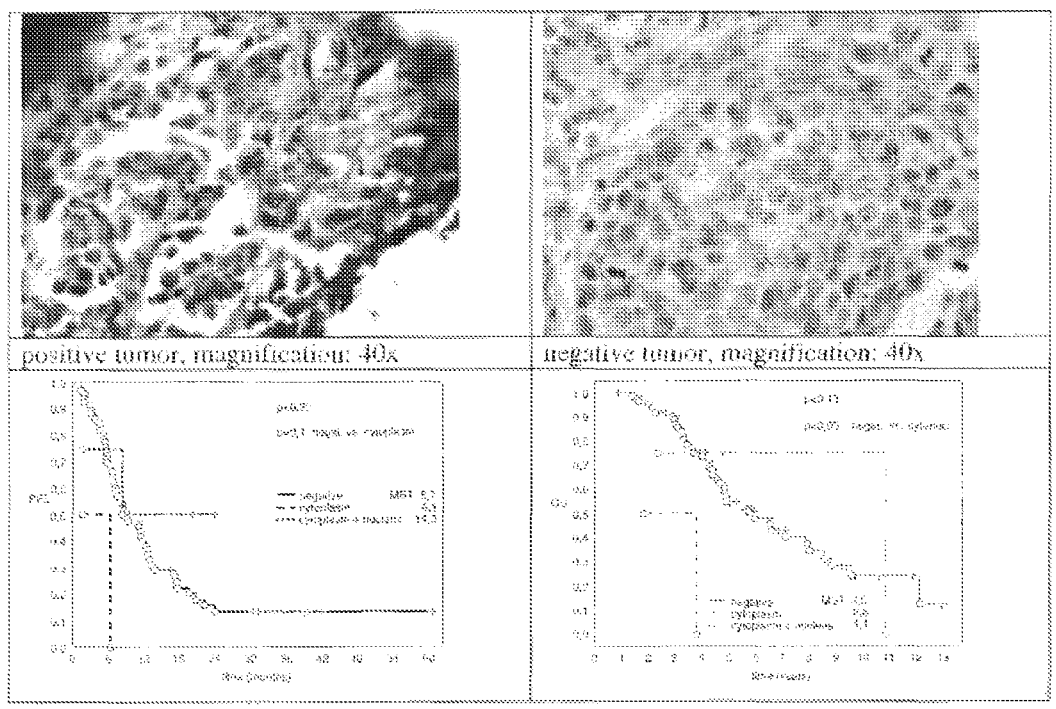

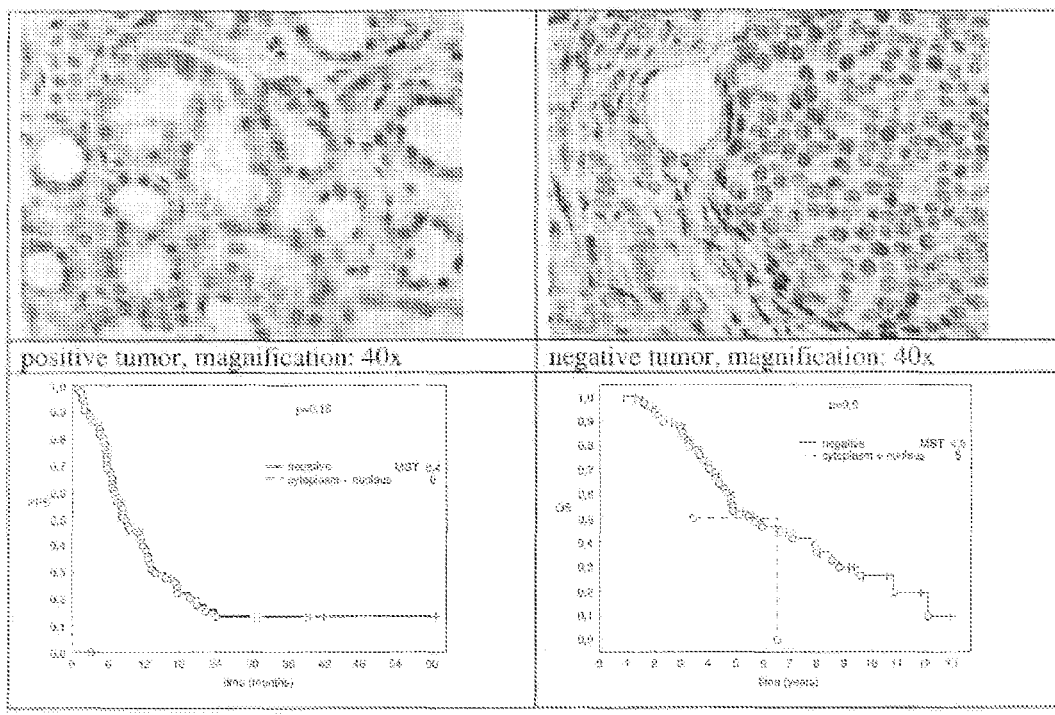
Fig. 4: Biomarker: pThr³⁰⁸ Act kinase; antibody: (244F9H2) rabbit mAb (Cell Signaling, USA)

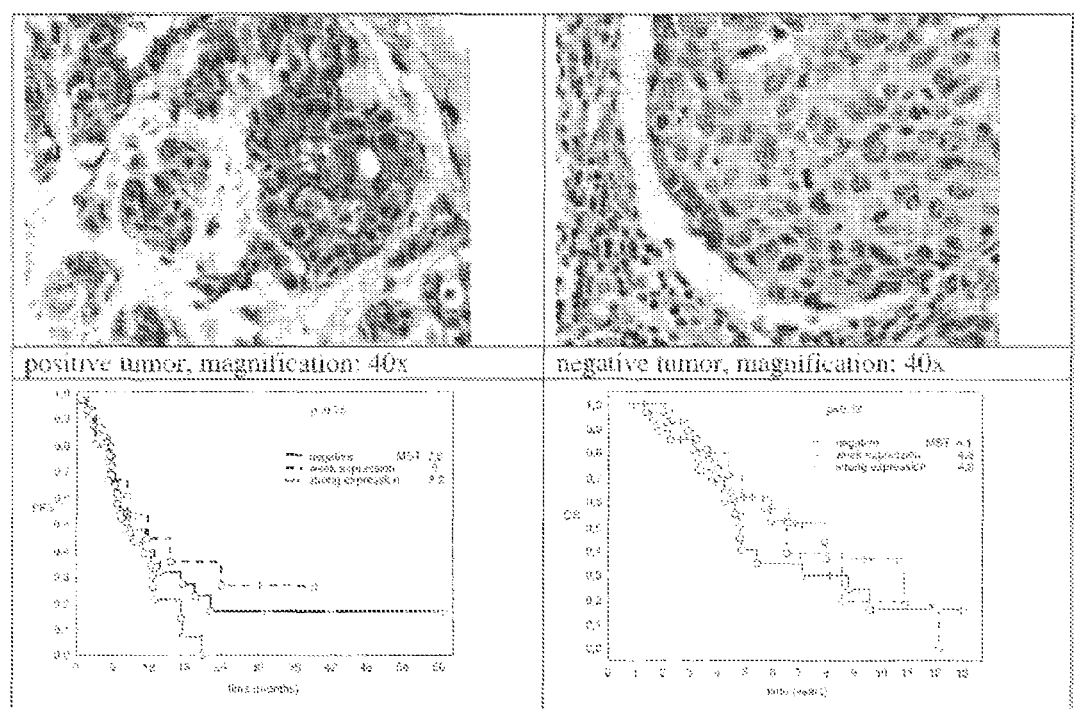
Fig. 5: Biomarker: total ERK 1/2 kinase; antibody: p44/42MAP rabbit mAb (Cell Signaling, USA)

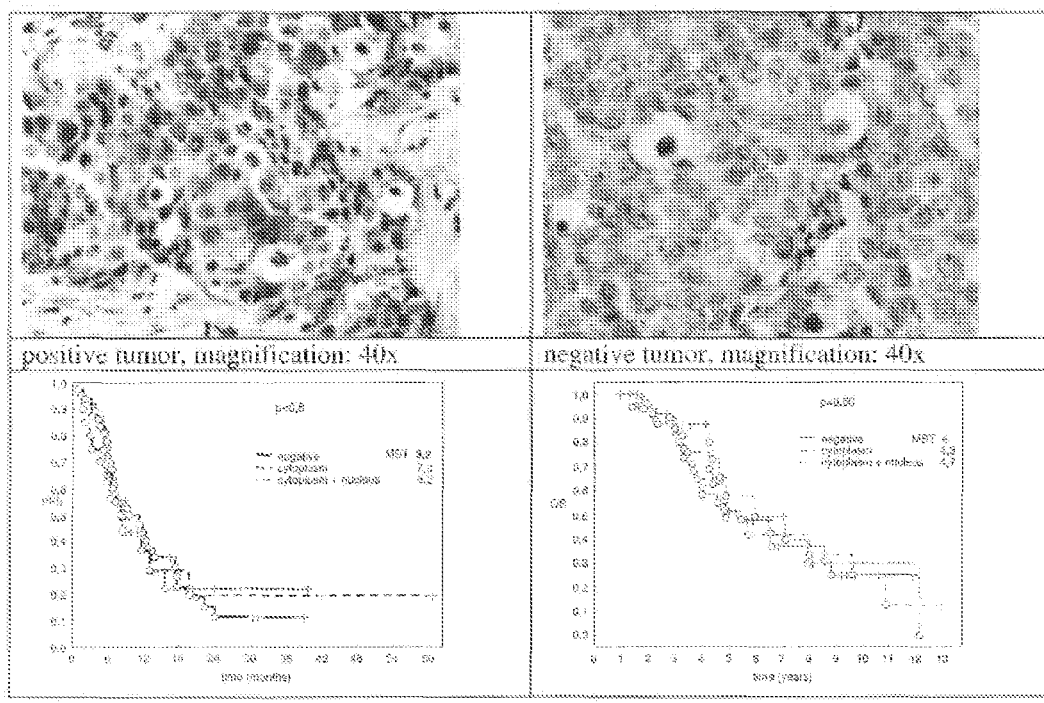
Fig. 6: Biomarker: pERK 1/2 kinase; antibody: p44/42MAPK (Thr202/Tyr204) (20G11) rabbit mAb (Cell Signaling, USA)

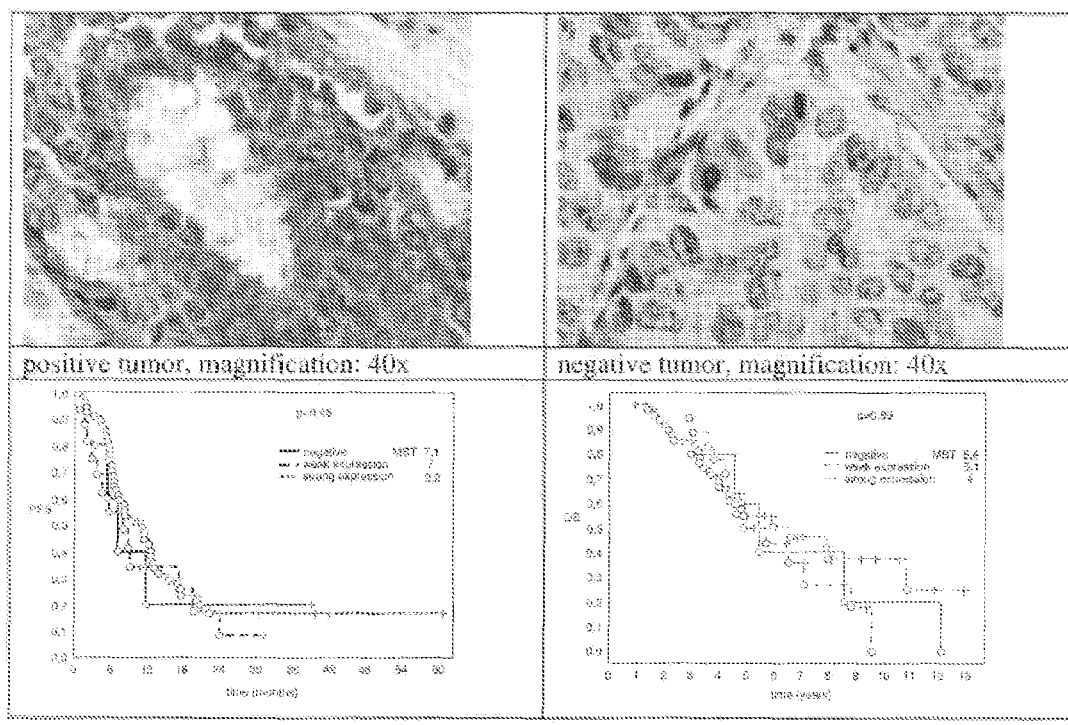

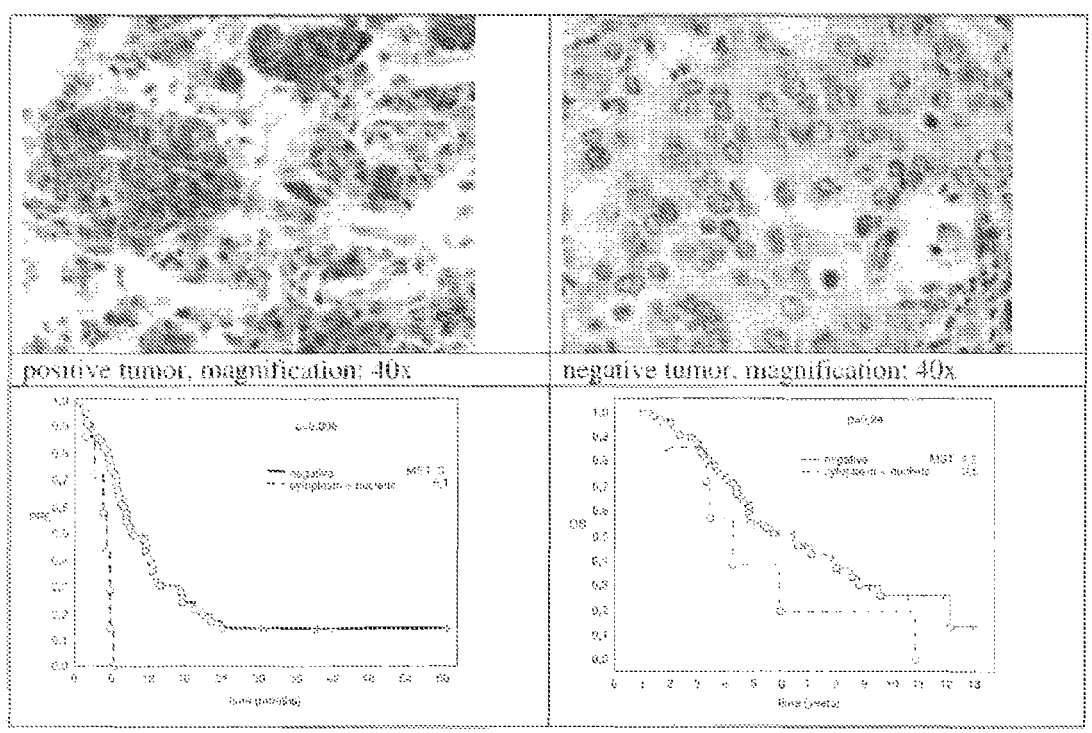

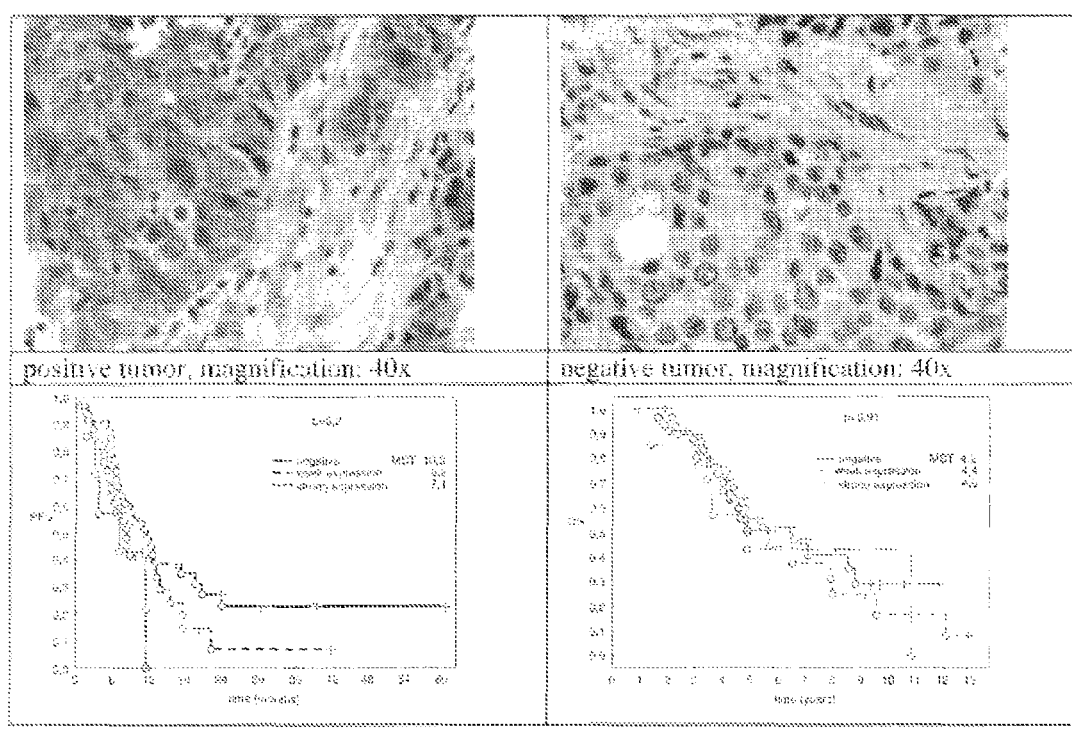

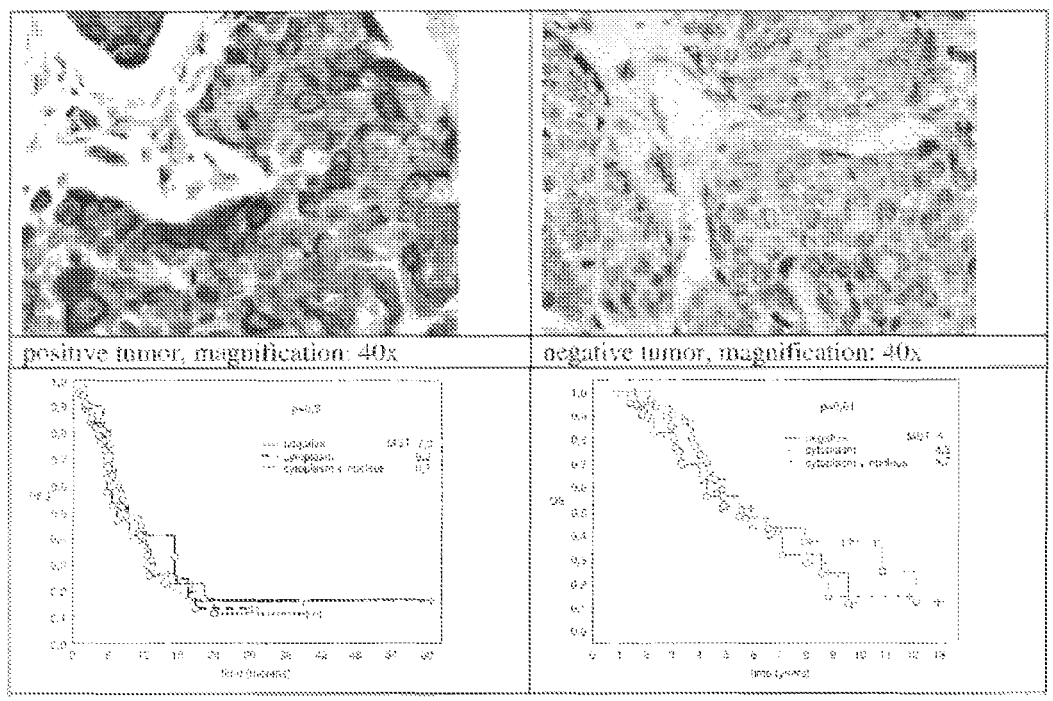
Fig. 10: Biomarker pSer2448 mTOR kinase: antibody (49F9) rabbit mAb (Cell Signaling, USA)

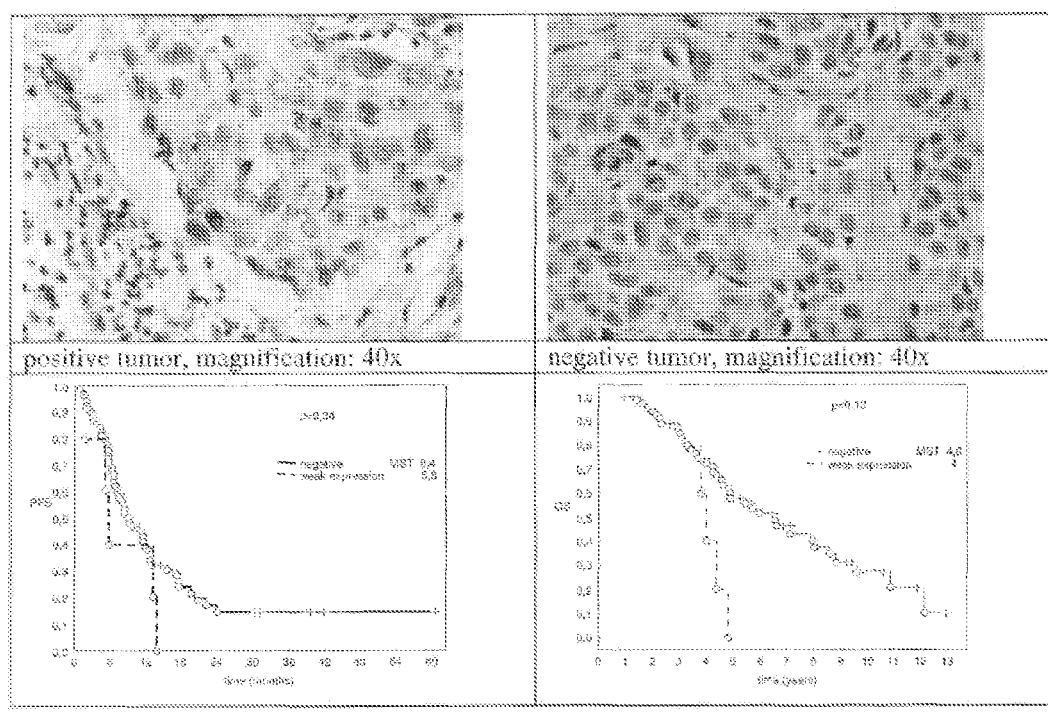
Fig. 11: Biomarker: total anti MUC4 protein; antibody: (1G8) mouse mAb (Zymed, USA)

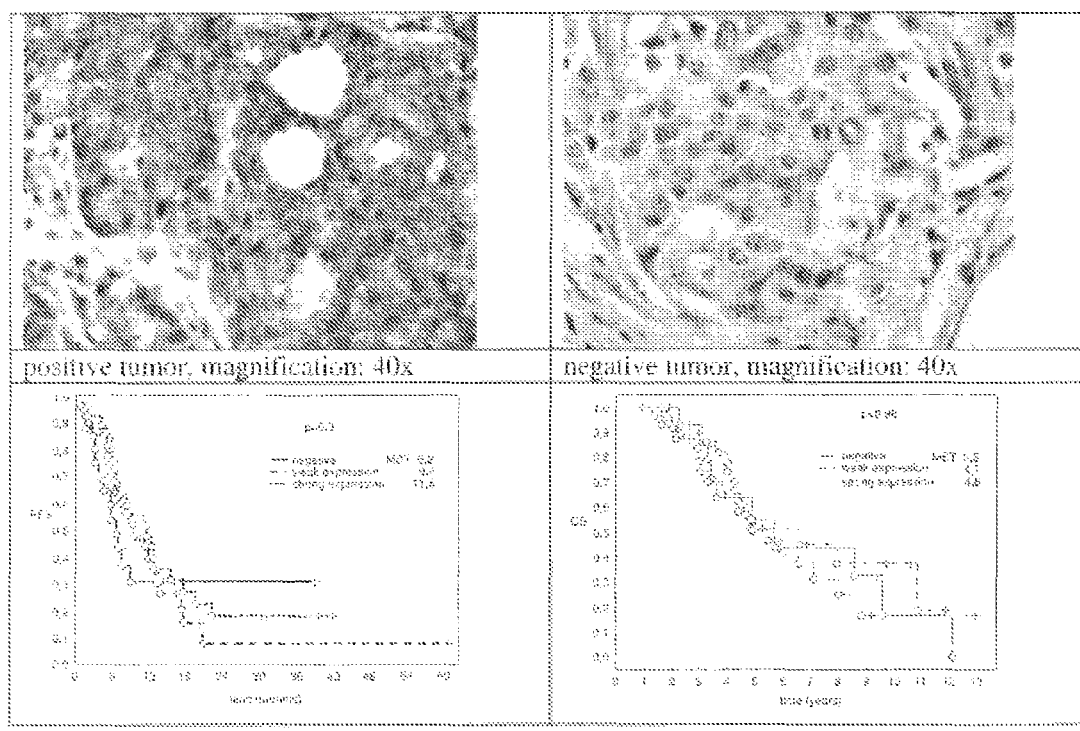

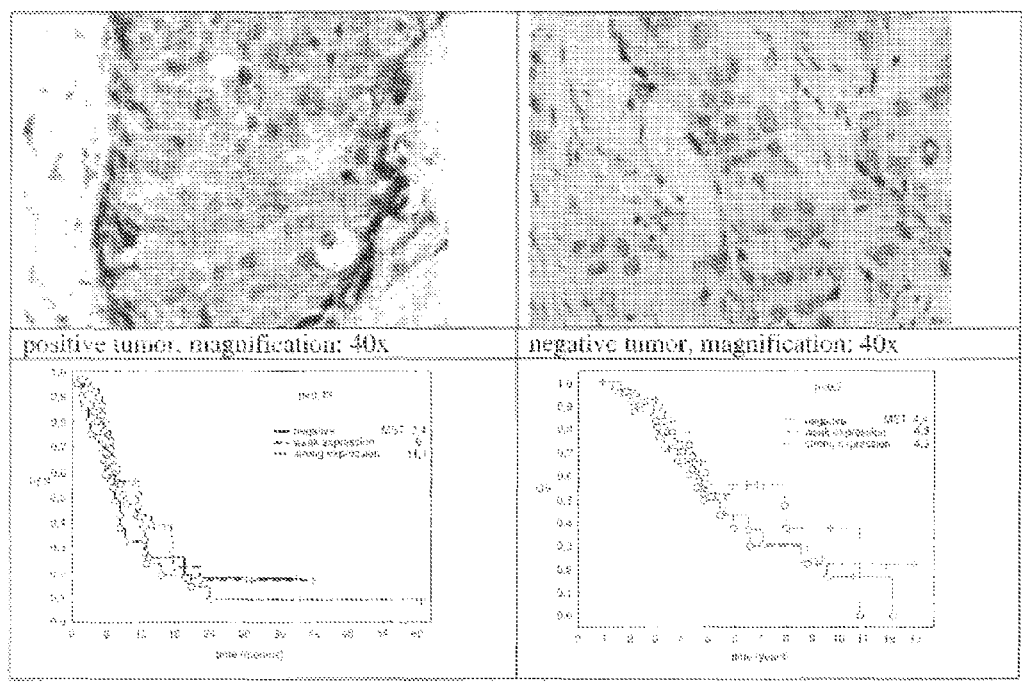
Fig. 13: Biomarker: total S6K protein; antibody: S6 Ribosomal Protein (5G10) rabbit mAb (Cell Signaling, USA)

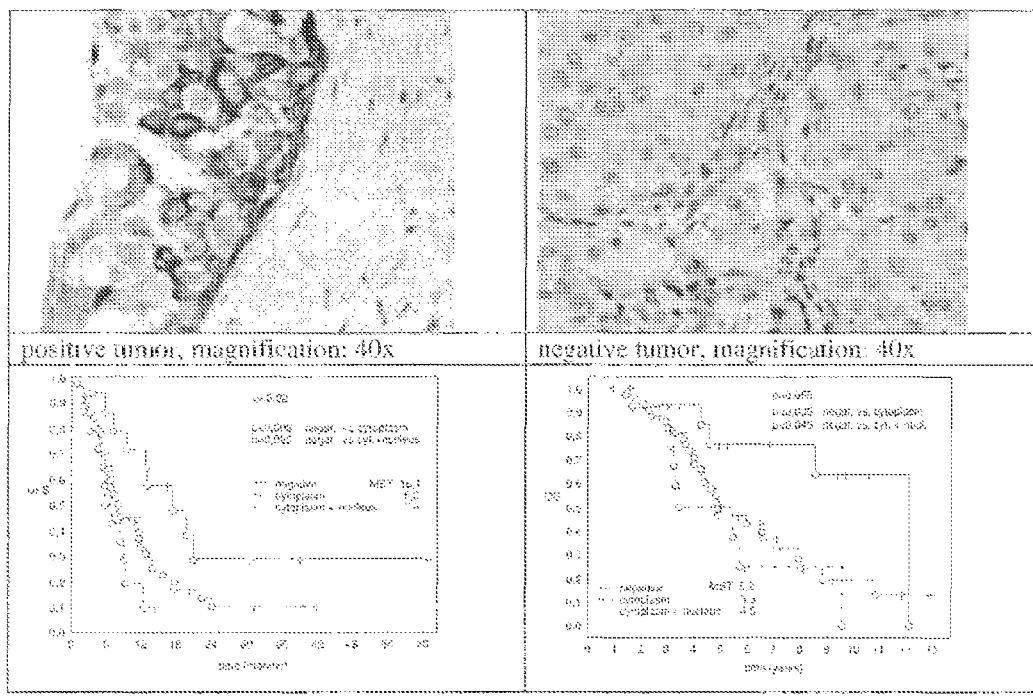
Fig. 14: Biomarker: pSer$^{235/236}$ S6K protein; antibody: phospho - S6 Ribosomal Protein (91B2) rabbit mAb (Cell Signaling, USA)

METHOD FOR DETERMINING THE SENSITIVITY OF PATIENTS SUFFERING FROM A CANCER DISEASE TO BIOLOGICAL THERAPY

FIELD OF THE INVENTION

The invention relates to a method for determining the sensitivity of patients suffering from a cancer disease to biological therapy based on the inhibition of HER receptor family signaling pathway.

BACKGROUND ART

Increasing incidence and costs of the treatment of malign tumors are a significant medical problem with direct and undesirable impact on the whole society. A typical example are the malignant neoplasia of the breast that represent the second most frequent malignancy in women living in developed countries. During the last 25 years the number of newly reported breast cancers in the Czech Republic increased almost twice. It ensues from the Czech National Oncology Registry (NOR) latest complete data that in 2004 the absolute number of new cases achieved 5628 patients, i.e., the incidence of 107.4 per 100 000 of women and the mortality of 40.06 per 100 000 of women (www.svod.cz). In approximately 20 to 25% of the patients the breast carcinoma shows an excessive expression of HER-2 receptor (hereinafter reported as HER-2 positive carcinomas) that usually originates on the basis of amplification of the gene. Those carcinomas are characterized by high degree of aggressiveness and, therefore, adverse prognosis. On the other hand, there exists an efficient therapy, targeted against the HER-2 receptor. It is for instance the monoclonal antibody trastuzumab that is indicated at present for adjuvant and palliative treatment of HER-2 positive breast carcinoma patients. In combination with chemotherapy this antibody brings, in case of adjuvant treatment, a significant decrease of the disease recurrence and, consequently, an increase of the number of cured patients, or a significant extension of life if administered to the patients with disseminated disease.

Despite the fact that trastuzumab is administered to a narrowly selected group of HER-2 positive carcinoma patients, the clinical response is variable, namely, both as to the tumor response and to period of duration. In general, it occurs in approximately 40% of the cases. The causes of resistance of the disease to trastuzumab are not determined unambiguously. It may be a damaging of HER-2 receptor that is not then capable of its own kinase activity or binding of the monoclonal antibody of trastuzumab. Altered may also be the individual signaling pathways of the HER-2 receptor or their regulators. Analogically to the targeted treatment directed at the HER-2 receptor, the problems of the need of rational indication of targeted treatment are solved in a similar manner also in the therapy directed at the other members of the HER gene family, e.g., HER-1 receptor and its inhibition by cetuximab, gefitineb or erlotinib. Those medicaments are indicated for other tumor diseases, e.g., cetuximab for HER-1 positive carcinoma of the colorectum, head and neck, or gefitinib or erlotinib for carcinoma of the lungs, pancreas and in other indications. The increasing number of clinical studies under progress documents high efficiency of the inhibitors directed to HER family in a number of clinical indications where the classical cytotoxic treatment is insufficiently efficient, nevertheless, not all patients benefit even from this targeted treatment and again, in case of the majority of roughly more than a half of the patients this treatment fails. With regard to high homology of the individual members of the HER family and similarity of their signaling pathways it is possible to assume that the efficiency biomarkers are similar.

DISCLOSURE OF THE INVENTION

The object of the present invention is a method for determining the sensitivity of a patient suffering from a cancer disease to biological therapy based on the inhibition of HER receptor family signaling pathway, performed with a biological material taken from the patient's body, wherein the expression of the biomarker S6 kinase or its post-translationally modified form or of S6 kinase activation biomarkers or their post-translationally modified forms is determined in the tumor. It was found that when the biomarker S6 kinase or its post-translationally modified form or the S6 kinase activation biomarkers or their post-translationally modified forms are expressed in a tumor, the tumor is resistant towards the biological therapy based on the inhibition of the HER receptor family signaling pathway, and, vice versa, when these biomarkers or their post-translationally modified forms are not expressed in a tumor, the tumor is sensitive to said biological therapy and the patient has a positive overall prognosis.

The biological therapy consists in the administration of a specific low-molecular (usually a synthetic organic molecule) or high-molecular (usually a protein, typically an antibody) inhibitor of cell-signaling, e.g.:

a) low-molecular HER-2 receptor inhibitors, such as lapatinib,
b) low-molecular inhibitors of other protein analogues of the HER family (e.g., HER-1, HER-3, HER-4), such as gefitinib, erlotinib,
c) high-molecular HER-2 receptor inhibitors, such as trastuzumab,
d) high-molecular inhibitors of other protein analogues of the HER family (e.g., HER-1, HER-3, HER-4), such as cetuximab or panitumumab.

It is an aspect of the invention that the biological material is a bioptic sample of the tumor or of another tissue or a body liquid, in which the presence of the tested biomarker can be determined.

In a preferred embodiment, the biomarkers of S6 kinase activation are selected from the group comprising co-regulated proteins, for instance but not limited to: ribosomal protein S6, protein eIF4B and IRS-1.

It is a further aspect of the invention that the cancer disease is a malign or a benign tumor of human or animal origin, preferably selected from the group comprising haemopoietic tumors, tumors of epithelial, mesenchymal and neuroectodermal origin, namely malign breast, colorectal, lung, pancreatic, head, neck, brain, prostate or skin neoplasms.

It is another aspect of the invention that the determination of the expression is performed using a detection method selected from the group comprising immunoanalytical methods, immunohistochemical methods, immunocytochemical methods, immunofluorescence techniques, enzyme analysis, radiometric analysis, scintigraphic analysis, positrone emission spectrometry, chemiluminiscence analysis, fluorimetric analysis, immunoprecipitation techniques and methods based on the principles of mass spectrometry.

S6 kinase 1 (synonymous to p70S6K, S6K1) is a serine/threonine kinase belonging to the S6K protein family (Jastrzebski K. at al., Growth Factors. 2007; 25 (4): 209-26, Mamane Y., et al., Oncogene. 2006; 25 (48): 6416-22, Manning B. M., J Cell Biol. 2004; 167 (3):399-403.). Human genome contains two different genes, encoding two forms of S6K: S6K1 and S6K2 (synonymous to S6 Kb). Both forms of S6K show a high degree of sequence homology and have a similar biological function. p70 or p85 forms of the S6K1 protein can be detected, based on post-translational modifications of S6K1. While p70 S6K1 (hereinafter referred to as S6K$^{p70}$) is found in cell cytoplasm, p85 S6K1 occurs in the nucleus. Similarly, there are two forms of the S6K2 protein, p54 and p56, both of them appear in the cell nucleus. The S6K1 encoding gene as well as the HER-2 receptor gene are found on chromosome 17. The amplification of the chromosomal region containing this gene and the excessive expression of S6K1 was found in many tumor cell lines, including breast carcinoma. In primary breast carcinomas, S6K1 is detected in 20 to 36% of cases; in HER-2 positive carcinomas in our set, the positivity of the expression of pSer$^{235/236}$ S6K1 occurred in up to 63% tumors. The negative expression was connected with good response to the therapeutic inhibition of HER-2 by trastuzumab with the time median to disease progression (progression-free survival, PFS) of 16.1 months in negative tumors and 6.3/7.8 months in the tumors positive in cytoplasm or in combined cytoplasmatic and nuclear positivity. These data show that almost all patients having tumors that show the S6K1 expression benefit only minimally from the therapeutic HER-2 gene inhibition.

S6K1 contains two different non-identical catalytic domains in the C-terminal part of the molecule, in the so-called T-loop kinase domain. The major function of S6K1 is phosphorylation of ribosomal S6 protein and eIF4B protein, thereby inducing proteosynthesis. Recent findings have shown that S6K1 also plays a role in the regulation of glucose metabolism by means of IRS-1 protein. The activity of S6K1 results in contributing to the increase of cell proliferation and survival. The anti-apoptotic effect of S6K1 is further increased by the regulatory activity of S6K to the Bcl-2 protein activity through the BAD protein phosphorylation.

S6K1 kinase is a part of the signaling pathway PI3K/AKT/mTOR (mammalian target of rapamycin), wherein it functions as the main effector of the signal transmission from mTOR. PI3K/AKT signaling pathway is activated as a result of the stimulation of growth factor receptors by their ligands. In case of HER-2 positive breast carcinoma it is namely by HER-2 receptor and also by EGFR, HER-3 and IGF-R receptors.

mTOR is activated by the action of PI3K and AKT kinases, which inhibit tuberous sclerosis proteins TSC1 and TSC2 that negatively regulate the mTOR activity. The ability of mTOR to phosphorylate (activate) S6K1 is further dependent on the formation of a protein complex composed of three proteins: rapamycin-sensitive adaptor protein, mTOR (raptor), G protein β-subunit-like protein (GβL) and prolin-rich substrate of 40 kDa protein-kinase B (PRAS40). This complex, designated "mTOR Complex1" (mTORC1) subsequently phosphorylates S6K1 on at minimum two protein residues, whereas namely the phosphorylation of threonine in the position 389 is essential for further functioning of S6K1, which induces the phosphorylation of further aminoacid residues on S6K1 by means of PDK1 kinase.

Our results show that the protein S6K is a promising predictive marker of the response of HER-2 positive breast carcinoma to the targeted trastuzumab therapy or to the therapy by another HER-2 receptor inhibitor. With regard to the similarity of the signaling pathways, it can be presumed that S6K may be the general predictive marker of response to the therapeutic inhibition of the signaling pathway of the HER receptor family.

In connection with all the herein shown data it is apparent that the diagnosis and therapy of malign tumors is an important medical issue with direct and undesirable impact on the whole society. Targeted anti-tumor therapy shows the above-mentioned advantages on one hand, however, on the other hand it brings a significant economic burden. The costs of using the targeted anti-tumor medicaments based on molecular antibodies commonly exceed the sum of one million Czech crowns per patient and year. The use of the detection of S6K for the prediction of the response to anti-tumor therapy targeted to the HER receptors may lead to rationalization of the therapy, to saving financial resources and to decreasing of unnecessary stress in those patients, whose probability of therapeutic benefits from the HER inhibition is minimal. Furthermore, the patients with S6K positive tumor may be provided with another, more effective therapies.

BRIEF DESCRIPTION OF DRAWINGS

The figures show for each biomarker examples of immunohistochemical determination of the individual biomarker expression in tumors using the light microscopy according to example 1, one microphotograph of the breast tumor with biomarker expression (positive tumor) and one microphotograph of the tumor without biomarker expression (negative tumor). Depicted further in the figures is the result of biostatic assessment of the significance of the expression (total or in cellular compartments: nucleus, cytoplasm or in their combination) of the biomarker concerned in the context of the length of the therapeutic efficiency of trastuzumab assessed by the progression-free survival time, PFS (cumulative survival on the y axis and time in months on the x axis); and overall survival, OS (cumulative survival on the y axis and time in years on the x axis); MST=mean survival time (months/years); level of statistical significance (p) assessed by long-rank test according to example 2.

FIG. 1: Biomarker: total Act (pan) kinase; antibody: (11E7) rabbit mAb (Cell Signaling, USA)

FIG. 2: Biomarker: pSer$^{473}$ Act kinase; antibody: (587F11) mouse mAb (Cell Signaling, USA)

FIG. 3: Biomarker: pSer/Thr Act kinase; antibody: substrate, rabbit mAb (Cell Signaling, USA)

FIG. 4: Biomarker: pThr$^{308}$ Act kinase; antibody: (244F9H2) rabbit mAb (Cell Signaling, USA)

FIG. 5: Biomarker: total ERK ½ kinase; antibody: p44/42MAP rabbit mAb (Cell Signaling, USA)

FIG. 6: Biomarker: pERK ½ kinase; antibody: p44/42MAPK (Thr202/Tyr204) (20G11) rabbit mAb (Cell Signaling, USA)

FIG. 7: Biomarker: total GSK3β kinase; antibody: (27C10) rabbit mAb (Cell Signaling, USA)

FIG. 8: Biomarker: pSer$^9$ GSK3β kinase; antibody: rabbit mAb (Cell Signaling, USA)

FIG. 9: Biomarker: total mTOR kinase; antibody: (7C10) rabbit mAb (Cell Signaling, USA)

FIG. 10: Biomarker: pSer$^{2448}$ mTOR kinase; antibody: (49F9) rabbit mAb (Cell Signaling, USA)

FIG. 11: Biomarker: total anti MUC4 protein; antibody: (1G8) mouse mAb (Zymed, USA)

FIG. 12: Biomarker: total PTEN protein; antibody: (138G6) rabbit mAb (Cell Signaling, USA)

FIG. 13: Biomarker: total S6K protein; antibody: S6 Ribosomal Protein (5G10) rabbit mAb (Cell Signaling, USA)

FIG. 14: Biomarker: pSer$^{235/236}$ S6K protein; antibody: phospho—S6 Ribosomal Protein (91B2) rabbit mAb (Cell Signaling, USA)

EXAMPLES OF CARRYING OUT THE INVENTION

Example 1

Immunohistochemical Determination of Biomarker Expression

Used for the immunohistochemical detection may be bioptic materials processed and sliced using various technique, most frequently formalin fixed tissues embedded in paraffin. The immunohistochemical reaction represents the visualization of the binding of the tissue antigen with the primary antibody. According to the particular method used it is also followed by the specific reaction of the secondary, or tertiary antibody, as the case may be, or another signal-amplifying system. Depending on the type of the used label, most frequently enzyme label, the antigen is visualized by the relevant chromogene at the point where the specific binding occurs. The binding of the antigen with the antibody proceeds without visible reaction. In order to enable the observation of the preparation by common methods of light or fluorescent microscopy, for the visualization of antigen localization and molecules bound to it, the so-called chromogenes or fluorochromes must be used. FITC (fluorescein-isothiocyanate) is most frequently used in immunofluorescence. In immunoenzyme reactions the antibodies are labeled by the conjugation with enzyme, e.g., horse-radish peroxidase or alkaline phosphatase. For the localization of positive structures in tissue context, the counterstaining of sections, e.g., by haematoxylin or fluorescent dyes of Hoechst type, is used frequently in immunohistochemistry or immunofluorescence.

After cutting the tissues and their optional de-paraffinization by standard procedures, the blocking of non-specific binding sites is performed by incubation in 0.5 ml per slide of blocking solution (e.g., 3% fat-free milk in Tris buffered saline pH 7.2-7.4, TBS) usually for 1 hour at room temperature. After pouring off the blocking solution the slides are rinsed shortly 2× in TBS. An appropriately diluted primary antibody was applied usually in concentration 1-10 µg/ml either in blocking solution, or in another suitable vehicle recommended by the manufacturer. The slides were incubated in a moist chamber usually for 2 hours at room temperature or overnight in the refrigerator. Subsequently, the primary antibodies were washed off by quick rinsing 2× in TBS and the sample was then incubated 3× for 5 minutes in TBS, while stirring slightly in the shaker. Then an appropriately diluted secondary antibody labeled, e.g., by peroxidase, was applied, usually again in blocking solution. At room temperature, the sample was incubated in moist chamber for 10-60 minutes. Subsequently the secondary antibodies were washed off by quick rinsing 2× in TBS and then incubate 3× for 5 minutes in TBS, mixing slightly in the shaker. Finally, the slides were poured over with freshly prepared substrate chromogen solution, e.g., with the content of diaminobenzidin (10 mg/ml and 0.3% hydrogen peroxide) in case of using detection system based on peroxidase for the period of 10-20 minutes. The reaction was stopped by pouring off the substrate solution and rinsing 2× in TBS. The preparations were counterstained by haematoxylin solution usually for 1 minute and rinsed in tap water. The preparation was dehydrated, mounted in and observed under a light microscope. The percentage of positive cells in the target population, or subcellular localization of the antigen (e.g., cytoplasm versus nuclear positivity) were analyzed semi-quantitatively. The results were assessed as follows: 1. negative, if less than 5-10 percent of cells in the target population are positive, 2. slightly positive, if more than 10 and less than 50 percent of cells in the target population are positive, and 3. strongly positive, if more than 50 percent of cells in the target population are positive. The results of the examinations for the individual biomarkers (total Act kinase, $pSer^{473}$ Act kinase, pSer/Thr Act kinase, $pThr^{308}$ Act kinase, total ERK½ kinase, $pThr^{202}/Tyr^{204}$ ERK½ kinase, total GSK3β kinase, $pSer^9$ GSK3β kinase, total mTOR kinase, $pSer^{2448}$ mTOR kinase, MUC4 protein, total PTEN protein, total S6K protein, $pSer^{235/236}$ S6K kinase) are shown in FIGS. 1-14.

Example 2

Biostatistic Assessment of Individual Biomarkers

In 2004 to 2007 we worked on a research project supported by the Internal Grant Agency of the Ministry of Health of the Czech Republic (NR8335) and the Ministry of Industry of the Czech republic (MPO 1H-PK/45) the aim of which was to explain which mechanisms cause resistance to trastuzumab and to develop new diagnostic tools for breast cancer. Within the framework of those projects we determined the occurrence and activity of approximately 20 different proteins in primary HER-2 positive breast carcinomas in 140 women, wherein one half of these patients were treated by the targeted biological treatment, trastuzumab. Our results demonstrate unambiguously that one of the monitored proteins, namely S6 kinase 1 (S6K1), is a strong predictor of the disease resistance to trastuzumab. Moreover, it is a biomarker with sufficient frequency of positivity (penetration) in the population of HER-2 positive tumors and thus it enables to predict, with high accuracy, the response to HER-2 inhibition therapy, even if utilized as a single-gene predictor.

Used as an example for the validation of the clinical significance of the individual markers was a group of female patients with the diagnosis of advanced HER-2 positive breast cancer treated by trastuzumab whose tumors were examined for the evaluated biomarkers (total Act kinase, $pSer^{473}$ Act kinase, pSer/Thr Act kinase, $pThr^{308}$ Act kinase, total ERK½ kinase, $pThr^{202}/Tyr^{204}$ ERK½ kinase, total GSK3β kinase, $pSer^9$ GSK3β kinase, total mTOR kinase, $pSer^{2448}$ mTOR kinase, MUC4 protein, total PTEN protein, total S6K protein, $pSer^{235/236}$ S6K kinase). Used as clinical variables were the progression-free survival (PFS), and overall survival (OS) in months/years. The progression-free survival is determined as the time from the beginning of the treatment to the confirmed progression of disease or the date of last contact with the patient. Overall survival is the time from the diagnosis to the death or the last contact. The curves of survival were created by means of Kaplan-Meier method (Kaplan, J Am Stat Assoc 1958). For the identification of risk factors associated with the progression-free survival and overall survival, univariation analysis was performed. The difference between the curves of survival was compared by means of log rank test (Peto, J R Stat Soc 1972). In the univariation analysis the following factors were assessed: positivity of immunohistochemical staining, mean time of survival (MST) to the disease progression and overall survival of the patients (both in months). The results of the statistical assessment for the individual biomarkers (total Act kinase, $pSer^{473}$ Act kinase, pSer/Thr Act kinase, $pThr^{308}$ Act kinase, total ERK½ kinase, $pThr^{202}/Tyr204$ ERK½ kinase, total GSK3β kinase, $pSer^9$ GSK3β kinase, total mTOR kinase, $pSer^{2448}$ mTOR kinase, MUC4 protein, total PTEN protein, total S6K protein, $pSer^{235/236}$ S6K kinase) are shown in FIGS. 1-14.

INDUSTRIAL APPLICABILITY

By the method according to the invention it is possible to predict, from the group of cancer patients indicated for the treatment by the inhibitors of the HER signaling pathways only those for whom that treatment most probably will be beneficial. The thus individualized therapy brings the optimization of the treatment costs and the patients are not burdened by inefficient treatment that represents for them an undesirable toxicity and a decrease of the quality of the life.

The invention claimed is:

1. A method for determining the sensitivity of a breast cancer patient to trastuzumab therapy comprising:
    (a) obtaining a breast tumor tissue sample;
    (b) measuring the level of S6Kinase 1 (S6K1) protein or the level of S6K1 phosphorylation at $Serine^{235/236}$ in the sample; and
    (c) identifying the patient as sensitive to trastuzumab therapy when the sample is negative for S6K1 protein expression or phosphorylation at $Serine^{235/236}$, and identifying the patient as resistant to trastuzumab therapy when the sample is positive for S6K1 protein expression or phosphorylation at $Serine^{235/236}$.

* * * * *